United States Patent [19]

Ishizuka et al.

[11] Patent Number: 6,160,017
[45] Date of Patent: Dec. 12, 2000

[54] PREVENTIVES AND REMEDIES FOR ULCEROUS COLITIS AND/OR CROHN'S DISEASE

[75] Inventors: Masaaki Ishizuka, Mishima; Kenji Maeda; Tomio Takeuchi, both of Tokyo; Tadayoshi Shiraishi, Hyogo; Masakazu Fukushima, Hanno, all of Japan

[73] Assignees: Zaidan Hojin Biseibutsu Kagaku Kenkyu Kai; Taiho Pharmaceutical Co., Ltd., both of Tokyo, Japan

[21] Appl. No.: 09/402,534

[22] PCT Filed: Apr. 8, 1998

[86] PCT No.: PCT/JP98/01614

§ 371 Date: Feb. 14, 2000

§ 102(e) Date: Feb. 14, 2000

[87] PCT Pub. No.: WO98/44916

PCT Pub. Date: Oct. 15, 1998

[30] Foreign Application Priority Data

Apr. 9, 1997 [JP] Japan .................................. 9-090688

[51] Int. Cl.$^7$ .................................................. A61K 31/195
[52] U.S. Cl. ............................ 514/563; 514/885; 514/925; 514/926
[58] Field of Search ........................................ 514/563, 885, 514/925, 926

[56] References Cited

U.S. PATENT DOCUMENTS 5,952,380   9/1999   Ishizuka et al. ...................... 514/563

FOREIGN PATENT DOCUMENTS 0 783 884      7/1997   European Pat. Off. ..... A61K 31/195
96/11681/A1    4/1996   WIPO .

OTHER PUBLICATIONS

Kawatsu, M. et al., "Improvement of intestinal toxicity of 5–fluorouracil by conagenin, a low molecular immunomodulator" Anticancer Res. 1996, vol. 16, No. 5A, pp. 2937 to 2941.

Kawatsu, M. et al., "Modulation by conagenin of inflammatory mediator productions in mice given 5–fluorouracil" Anticancer Res. 1997, vol. 17, No. 2A, pp. 917 to 922.

International Search Report.

*Primary Examiner*—Frederick Krass
*Attorney, Agent, or Firm*—Sughrue, Mion, Zinn, Macpeak & Seas, PLLC

[57] ABSTRACT

The invention relates to an agent for preventing and treating ulcerous colitis and/or Crohn's disease, comprising conagenin or a pharmaceutically acceptable salt thereof as an active ingredient. According to the present invention, there is provided an agent for preventing and treating ulcerous colitis and/or Crohn's disease, which has high therapeutic effect and safety.

2 Claims, No Drawings

PREVENTIVES AND REMEDIES FOR ULCEROUS COLITIS AND/OR CROHN'S DISEASE

This application is a 371 of PCT/JP 98/01614, filed Apr. 8, 1998.

TECHNICAL FIELD

The present invention relates to a medicament useful in preventing and treating ulcerous colitis and/or Crohn's disease.

BACKGROUND ART

Ulcerous colitis and Crohn's disease are designated to specific intractable diseases by the Ministry of Health and Welfare who prescribes, as a treating method for ulcerous colitis, the administration of salazosulfapyridine and prednisolone while adjusting their doses according to the condition of a patient (Annual Report of Refractory Inflammatory Bowel Disease Research Group of Ministry of Health and Welfare, 1988, 38), and as a treating method for Crohn's disease, the massive administration of an adrenocortical hormone for a small intestine type disease and of salazosulfapyridine for a large intestine type disease at an active phase, and the usual administration of salazosulfapyridine at a remissive phase (Annual Report of Refractory Inflammatory Bowel Disease Research Group of Ministry of Health and Welfare, 1990, 34). However, salazosulfapyridine often causes a side effect and hence involves a problem of patients who cannot be tolerant of prolonged administration (intolerant patients). Besides, prednisolone also involves a problem that prolonged administration becomes difficult by a side effect caused by the reason that it is a steroid.

Mesalazine has been developed for alleviating this side effect. However, the incidence rate of the side effect has been somewhat lowered, but not that the side effect has completely vanished. There is no great difference in clinical effect, and so it is hard to say that the problems have been satisfactorily solved. By the way, the results of a double blind test [Japanese Pharmacology & Therapeutics, Vol. 22, supplement, pp. S2555–S2583 (1994)] on mesalazine using salazosulfapyridine as a control were such that the generalized amelioration rate is 68.8% for mesalazine, or 63.5% for salazosulfapyridine, and the incidence rate of the side effect is 11.5% for mesalazine, or 28.1% for salazosulfapyridine.

With respect to the cause of inflammatory intestinal diseases, there have hitherto been many unknown points. However, the cytokine analysis of the tissue of the diseased part of a patient and research on cytokine production by immunocompetent cells have suggested that inflammatory cytokines such as IL-1α, TNF-α, IL-6 and IL-8 strongly participate in the formation and progress of morbidity [Gastroenterology, Vol. 106, pp. 533–539 (1992); Lancet, pp. 2434–2340 (1992)], thus leading to the consideration that the inflammatory intestinal diseases are tissue damages caused by inflammatory cytokines produced at an abnormally high level from immunocompetent cells. In recent years, an anti-cytokine therapy by administration of a TNF-α-chimera antibody [Gastroenterology, Vol. 109, pp. 129–135 (1995)] or rectal administration of IL-10 [Gastroenterology, Vol. 108, pp. 1434–1444 (1995)] has been attempted as a new attempt. However, this therapy has involved a problem that the treatment is not simple, and high in cost.

Accordingly, it is an object of the present invention to provide an agent for preventing and treating ulcerous colitis and/or Crohn's disease, by which the problem of the side effect attendant on the treatment with salazosulfapyridine or a steroidal agent is overcome, the problems of therapeutic facility and treatment cost in the therapy with the TNF-α-chimera antibody and the therapy by the rectal administration of IL-10 are solved, and a high therapeutic effect can be achieved.

DISCLOSURE OF THE INVENTION

With the foregoing circumstances in view, the present inventors have made research on various kinds of medicaments using inflammatory intestinal disease models such as i) acetic acid-induced models, ii) trinitrobenzenesulfonic acid-induced models and iii) dextran sulfate-induced models [Scand J Gastroenterol, Vol. 27, pp. 529–537 (1992)]. As a result, it has been found that conagenin is useful as an agent for preventing and treating ulcerous colitis and Crohn's disease, thus leading to completion of the present invention.

Namely, the present invention is directed to an agent for preventing and treating ulcerous colitis and/or Crohn's disease, comprising conagenin or a pharmaceutically acceptable salt thereof as an active ingredient.

The present invention is also directed to a medicinal composition for preventing and treating ulcerous colitis and/or Crohn's disease, comprising conagenin or a pharmaceutically acceptable salt thereof and a pharmaceutically acceptable carrier.

The present invention is further directed to use of conagenin or a pharmaceutically acceptable salt thereof for the preparation of an agent for preventing and treating ulcerous colitis and/or Crohn's disease.

The present invention is still further directed to a method of preventing and treating ulcerous colitis and/or Crohn's disease, which comprises administering an effective amount of conagenin or a pharmaceutically acceptable salt thereof to a patient.

BEST MODE FOR CARRYING OUT THE INVENTION

Conagenin is a compound represented by the following structural formula, and termed "(2S)N-[(2R,3S,4R)2,4-dihydroxy-3-methyl-pentanoyl]-2-methylserine" in nomenclature.

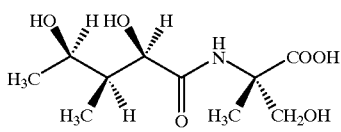

Conagenin is a publicly known compound and is described about the properties of matter and preparation process thereof in Japanese Patent Application Laid-Open No. 306953/1990 by the present inventors, about its use for the treatment for thrombocytopenia or leukocytopenia in Japanese Patent Application Laid-Open No. 229939/1993, about its use for an agent for alleviating the side effect attendant on cancer chemotherapy and/or radiotherapy in Japanese Patent Application Laid-Open No. 65072/1994, and about its use for the prevention and treatment of diarrhea in Japanese Patent Application Laid-Open No. 165236/1996. However, nothing has been known about the effect of conagenin on ulcerous colitis and/or Crohn's disease.

In the present invention, no particular limitation is imposed on the salt of conagenin so far as it is a pharmaceutically acceptable salt. Examples thereof include metal salts of the carboxyl group in conagenin, particularly, salts with alkali metals such as sodium and potassium and salts with alkaline earth metals such as calcium and magnesium, and an ammonium salt.

Conagenin can be collected from cultures of a conagenin-producing strain belonging to the genus Streptomyces, and can be obtained in accordance with, for example, the preparation process described in Japanese Patent Application Laid-Open No. 306953/1990.

Conagenin has low toxicity. For example, in an acute toxicity test on rats, the $LD_{50}$ value of conagenin was observed at a level of 500 mg/kg or more irrespective of variant routes such as oral administration, subcutaneous administration, intraperitoneal administration and intravenous administration.

The agent for preventing and treating ulcerous colitis and/or Crohn's disease according to the present invention can be prepared as a medicinal composition by blending a proper amount of conagenin or a pharmaceutically acceptable salt thereof with carriers for preparations generally used. As the carriers, there may be used various kinds of pharmaceutically acceptable carriers commonly used, for example, excipients, binders, disintegrators, lubricants, colorants, taste corrigents, smell corrigents, surfactants, etc. No particular limitation is imposed on the preparation form of the agent for preventing and treating ulcerous colitis and/or Crohn's disease according to the present invention, and the form may be suitably determined according to the purpose thereof. However, specific examples thereof include oral forms such as tablets, coated tablets, pills, powder, granules, grains, capsules, solutions, suspensions and emulsions; and parenteral forms such as injections, suppositories, ointments, hard ointments, plasters and aerosol. These forms can be prepared in accordance with a method known per se in the art.

The tablets may be prepared by using, as carriers, for example, an excipient such as lactose, sucrose, sodium chloride, glucose, urea, starch, calcium carbonate, kaolin, crystalline cellulose or silicic acid; a binder such as simple syrup, glucose solution, starch solution, gelatin solution, carboxymethyl cellulose, shellac, methyl cellulose, potassium phosphate or polyvinyl pyrrolidone; a disintegrator such as dry starch, sodium alginate, agar powder, laminaran powder, sodium bicarbonate, calcium carbonate, polyoxyethylene sorbitan fatty acid ester, sodium lauryl sulfate, stearic acid monoglyceride, starch or lactose; a disintegration-preventing agent such as sucrose, stearic acid, cacao butter or hydrogenated oil; an absorbefacients such as a quaternary ammonium salt or sodium lauryl sulfate; a humectant such as glycerol or starch; an adsorbent such as starch, lactose, kaolin, bentonite or colloidal silica; and a lubricant such as purified talc, stearic acid salt, boric acid powder or polyethylene glycol to tablet the resultant medicinal composition in accordance with a method known per se in the art. The tablets may be provided as tablets coated with usual coatings, for example, sugar-coated tablets, gelatin-coated tablets, enteric coated tablets, film-coated tablets, double layer tablets, multilayer-coated tablets and the like as needed.

The pills may be prepared by using, as carriers, for example, an excipient such as glucose, lactose, starch, cacao butter, hardened vegetable oil, kaolin or talc; a binder such as gum arabic powder, tragacanth gum or gelatin; and a disintegrator such as laminaran or agar in accordance with a method known per se in the art.

The capsules are prepared by mixing the compound according to the present invention with the various carriers exemplified above and charging the mixture into hard gelatin capsules, soft capsules or the like.

An oral liquid form such as a solution, syrup or elixir may also be prepared by adding carriers such as a taste corrigent, a buffer, a stabilizer and a smell corrigent to the active ingredient in accordance with a method known per se in the art. In this case, there may be used sucrose, orange peel, citric acid, tartaric acid or the like as the taste corrigent, sodium citrate or the like as the buffer, and tragacanth gum, gum arabic, gelatin or the like as the stabilizer.

In the case where the injections are prepared, the resulting solutions, emulsions and suspensions must be sterilized and are preferably isotonic with blood. As a diluent used in the preparation thereof, may be used, for example, water, ethyl alcohol, macrogol, propylene glycol, ethoxylated isostearyl alcohol, polyoxylated isostearyl alcohol or polyoxyethylene sorbitan fatty acid ester. In this case, sodium chloride, glucose or glycerol may be contained in an amount sufficient to prepare an isotonic solution in the medicinal preparations. Besides, a pH adjustor, a buffer, a stabilizer, a local anesthetic and the like may be added. Examples of the pH adjustor and buffer include sodium citrate, sodium acetate, sodium phosphate and sodium bicarbonate, and examples of the stabilizer include sodium pyrosulfite, ethylenediaminetetraacetic acid, thioglycolic acid and thiolactic acid. Examples of the local anesthetic include procaine hydrochloride and lidocaine hydrochloride.

The suppositories can be prepared by adding a base, and optionally a surfactant and the like to the active ingredient according to the present invention in accordance with a method known per se in the art. Examples of the base used include oily bases such as lanolin, cacao butter, fatty acid triglycerides and Witepsol (product of Dynamit Nobel Co.), and water-soluble bases such as macrogol.

The ointments may be prepared by incorporating carriers such as a base, a stabilizer, a wetting agent and a preservative, which are routinely used, into the compound according to the present invention as needed, and mixing the components to formulate the desired preparations in accordance with a method known per se in the art. Examples of the base include liquid paraffin, white petrolatum, bleached bees wax, octyldodecyl alcohol and paraffin. Examples of the preservative include methyl p-hydroxybenzoate, ethyl p-hydroxybenzoate and propyl p-hydroxybenzoate.

The plasters may be prepared by applying the above-described ointment, paste, cream or gel to a support routinely used in accordance with a method known per se in the art. As the support, a fabric or nonwoven fabric made of cotton, rayon or chemical fibers, or a film or foamed sheet of soft polyvinyl chloride, polyethylene or polyurethane is suitable.

The above-described respective preparations may further contain colorants, preservatives, perfume bases, flavors, sweeteners, etc., and other medicaments as needed.

The amount of conagenin or a salt thereof contained in the medicinal preparations according to the present invention may be selected from a wide range without any particular limitation. However, it is normally preferred to contain it in a proportion of 0.2 to 90% by weight based on each medicinal preparation.

There is no particular limitation to administration routes of the above-described medicinal preparations, and the administration route may be suitably determined according to preparation forms, the age, sex and other conditions of a patient to be dosed, the condition of a disease to be treated, and the like. For example, the tablets, pills, granules, capsules, solution, suspension and emulsion are orally administered. The injection is intravenously administered singly or in combination with a usual supplemental solution containing glucose, amino acids and/or the like, and if needed, this administration is intramuscularly, intracutaneously, subcutaneously or intraperitoneally available with no combination use. The suppositories are intrarectally administered. The ointments are applied to the skin, oral mucosa membrane, etc.

The dose of conagenin is suitably determined according to the diseased condition, weight, age, sex and other conditions of a patient to be dosed, and the like. However, it is normally preferred that the parenteral dose be determined in the range of 0.1 mg to 5 g per day in terms of conagenin content and the oral dose in the range of 0.5 mg to 5 g. Meanwhile, the administration may be once per day, or may be divided into 2 to 4 times per day.

EXAMPLES

The present invention will hereinafter be described in more detail by the following examples.

Test Example 1
Effect on Acetic Acid-induced Rat Ulcer Model:

Morbid models were prepared by starving male Donryu:CRJ rats (aged 6 weeks; 9 rats per group) for 24 hours, incising each of their abdomens under etherization to ligate its colon, injecting a 10% aqueous solution (2 ml) of acetic acid into the digestive tract lumen thereof by means of a syringe equipped with a 25 G needle, further injecting air (3 ml) to discharge the acetic acid solution, and then suturing and closing the operated part. Conagenin was intravenously administered to the rats in a dose of 50 mg/kg 24 hours before the preparation of the models and right after the operation. After 24 hours, the rat models were slaughtered to take out their colons and recta. These organs were incised by 10 cm above from the anus to remove their contents. Thereafter, the weight of the organs was measured, and moreover the degree of mucosal disorder was visually observed. The degree of the tissue damage was evaluated using the grades "light", "medium" and "serious". The results are shown in Table 1.

TABLE 1

Suppressing effect of conagenin on enteritis in acetic acid-induced rat ulcer models

|  | Control group | | | Conagenin-dosed group | | |
|---|---|---|---|---|---|---|
| Grade of inflamation | Light (1) | Medium (2) | Serious (3) | Light (1) | Medium (2) | Serious (3) |
| Number of animals | 1 | 5 | 3 | 5 | 3 | 1 |
| Grade of inflammation, mean ± SD | 2.38 ± 0.67 | | | 1.50 ± 0.73 | | |

It is understood from Table 1 that the group dosed with conagenin exhibits a high suppressing effect on the inflammatory ulcer caused by the administration of acetic acid compared with the control group (group dosed with physiological saline).

Test Example 2

Effect on Trinitrobenzenesulfonic Acid-induced Ulcer Model:

Morbid models were prepared by starving male Wister rats (aged 6 weeks; 7 rats per group) for 48 hours, inserting a catheter by 8 cm through the anus of each of the rats under anesthesia with pentobarbital to inject a solution (0.25 ml) with 2,4,6-trinitrobenzenesulfonic acid dissolved in 50% ethanol in a proportion of 80 mg/ml, stopping the anus for about 10 minutes and then allowing it to stand.

Conagenin was intravenously administered to the rats in a dose of 50 mg/kg. Salazosulfapyridine was orally administered as a control agent in a dose of 300 mg/kg. The administration of these test agents was carried out every day from the day before the administration of 2,4,6-trinitrobenzenesulfonic acid to the fourth day after the administration. The rat models were slaughtered at the fifth day after the administration to determine a change in the wet weight of their recta (8 cm) and make a judgment on the basis of the pathological findings thereof.

The degree of the tissue damage was evaluated using the grades "no marked change", "light", "medium" and "serious". The results are shown in Tables 2 and 3.

TABLE 2

Suppressing effect of conagenin on inflammatory change (weight increase of large intestine) in trinitrobenzene-sulfonic acid (TNBS)-induced rat colitis models

| Administration group | Wet weight of large intestine (g) | Percent change in wet weight against untreated group (%) |
|---|---|---|
| Untreated group | 1.571 ± 0.161 | 100 |
| Group dosed with TNBS and physiological saline | 1.723 ± 0.167 | 110 |
| Group dosed with TNBS and conagenin | 1.572 ± 0.099 | 100 |
| Group dosed with TNBS and salazo-sulfapyridine | 1.641 ± 0.140 | 104 |

TABLE 3

Suppressing effect of conagenin on inflammatory pathological change of the intestinal tract in trinitrobenzenesulfonic acid (TNBS)-induced rat colitis models

| Grade | Untreated group | | | | Group dosed with TNBS and physiological saline | | | |
|---|---|---|---|---|---|---|---|---|
| | No marked change | Light | Medium | Serious | No marked change | Light | Medium | Serious |
| Pathological findings of colon | | | | | | | | |
| Findings of ulceration | 7 | | | | 3 | | 2 | 2 |
| Findings of depth of invasion | | | | | | | | |
| On *lamina propria mucosae* | 7 | | | | 3 | | 4 | |
| On submucosal tissue | 7 | | | | 3 | 2 | | 2 |
| On *tunica muscularis* | 7 | | | | 7 | | | |
| Inflammatory change | 7 | | | | 3 | 2 | 2 | |

| Grade | Group dosed with TNBS and conagenin | | | | Group dosed with TNBS and salazosulfapyridine | | | |
|---|---|---|---|---|---|---|---|---|
| | No marked change | Light | Medium | Serious | No marked change | Light | Medium | Serious |
| Pathological findings of colon | | | | | | | | |
| Findings of ulceration | 5 | 2 | | | 3 | 2 | 2 | |
| Findings of depth of invasion | | | | | | | | |
| On *lamina propria mucosae* | 5 | 2 | | | 3 | 2 | 2 | |
| On submucosal tissue | 7 | | | | 5 | 2 | | |
| On *tunica muscularis* | 7 | | | | 7 | | | |
| Inflammatory change | 6 | 1 | | | 4 | 2 | 1 | |

The numerals in the table all indicate the number of animals (rats).

With respect to the change in the wet weight of the large intestine (Table 2), which is correlated with the degree of inflammatory change, the increase was 10% in the control group (group dosed with physiological saline), whereas the increase was 4% in the group dosed with salazosulfapyridine which was used as the control agent. No increase was observed in the group dosed with conagenin.

With respect to the pathological findings (Table 3), the depth of invasion of the ulcer was medium in the group dosed with physiological saline and the group dosed with salazosulfapyridine in the judgment of the pathological findings on the lamina propria mucosae and submucosal tissue, whereas the depth of invasion was light in the group dosed with conagenin. Namely, it was confirmed that conagenin has a marked effect. With respect to the stage of lesion as well, 4 rats reached a subacute stage in the group dosed with physiological saline and the group dosed with salazosulfapyridine, whereas only 2 rats reached the subacute stage in the group dosed with conagenin. With respect to the inflammatory change as well, exactly the same good result was yielded in the group dosed with conagenin.

From the above-described results, it was proved that conagenin has a marked therapeutic effect compared with salazosulfapyridine which is a control agent.

Test Example 3

Single Administration Toxicity Test

Conagenin (500 mg/kg) was singly administered intravenously, intraperitoneally, subcutaneously or orally to mice and rats to investigate its toxicity. The results are shown in Table 4,

TABLE 4

Results of single administration toxicity test on conagenin

| Animal | Administration route | $LD_{50}$ (mg/kg) |
|---|---|---|
| Rat | Intravenous | >500 |
| | Intraperitoneal | >500 |
| | Subcutaneous | >500 |
| | Oral | >500 |
| Mouse | Intravenous | >500 |

No death was observed in both mice and rats administered, and no abnormal finding of general symptoms was also observed. From the above, it was confirmed that conagenin is a safe agent in single administration.

Test Example 4

Repeated Administration Toxicity Test

Conagenin (100 mg/kg) was intraperitoneally administered repeatedly for 3 months to male Wister rats (aged 6 weeks; 3 rats per group) to evaluate its toxicity using a group dosed with physiological saline as a control. Tests were made for general symptoms, urinalysis, blood test, blood biochemical test, autopsy, organ weight and pathological test. The results are shown in Table 5.

TABLE 5

Results of 3-month repeated administration toxicity test on conagenin by intraperitoneal administration to rats

| Group Test item | Group dosed with physiological saline (control) | Group dosed with conagenin |
| --- | --- | --- |
| Death | None | None |
| General symptoms | Normal | No marked change was observed compared with control |
| Hematological test | Normal | No marked change was observed compared with control |
| Blood biochemical test | Normal | No marked change was observed compared with control |
| Urinalysis | Normal | No marked change was observed compared with control |
| Pathological test | Normal | No marked change was observed compared with control |

The judgment of the test items was conducted in accordance with "Guideline of Toxicity Testing Methods".

With respect to all the items tested, i.e., general symptoms, urinalysis, blood test, blood biochemical test, autopsy, organ weight and pathological test, no significant change was observed in the group dosed with conagenin compared with the group dosed with physiological saline. Namely, it was confirmed that conagenin exhibits extremely high safety even in its repeated administration over a long period of time.

As a result of a repeated administration toxicity test for 13 weeks on rats, death cases, dying cases, etc. were observed in mesalazine, which is said to be excellent in safety compared with salazosulfapyridine, in doses of 200 and 400 mg/kg close to the efficacious dose [Oyo Yakuri (Pharmacometrics), Vol. 48, pp. 277–278 (1994)], whereas no development of toxicity was observed in conagenin in the efficacious dose of 100 mg/kg in the 3-month repeated administration toxicity test on rats. Namely, it was proved that conagenin has far higher safety compared with the existing drugs.

Example 1

Tablet Preparation

| | |
| --- | --- |
| Conagenin | 300 mg |
| Starch | 112 mg |
| Magnesium stearate | 18 mg |
| Lactose | 45 mg |
| One tablet contained | 475 mg. |

A tablet preparation was formulated in accordance with the above formulation and a method known per se in the art.

Example 2

Injection Preparation

| | |
| --- | --- |
| Conagenin | 50 mg |
| Distilled water for injection | q.s. |
| One ampule (dissolved upon use) contained | 5 ml. |

An injection preparation was formulated in accordance with the above formulation and a method known per se in the art.

Example 3

Suppository Preparation

| | |
| --- | --- |
| Conagenin | 300 mg |
| Witepsol W-35 (trade mark, product of Dynamite Nobel Co.) | 1400 mg |
| One suppository contained | 1700 mg. |

A suppository preparation was formulated in accordance with the above formulation and a method known per se in the art.

INDUSTRIAL APPLICABILITY

The agents for preventing and treating ulcerous colitis and/or Crohn's disease according to the present invention have a high therapeutic effect compared with the conventional agents, scarcely cause side effects and are extremely high in safety.

What is claimed is:

1. A method for treating ulcerous colitis and/or Crohn's disease, comprising administering to a host in need of such treatment an effective amount of conagenin or a pharmaceutically acceptable salt thereof.

2. The method according to claim 1, wherein said effective amount is an anti-inflammatory amount.

\* \* \* \* \*